United States Patent [19]

Kemp et al.

[11] Patent Number: 5,120,896

[45] Date of Patent: Jun. 9, 1992

[54] CONCURRENT ISOMERIZATION AND DISPROPORTIONATION OF OLEFINS

[75] Inventors: Richard A. Kemp, Stafford; David M. Hamilton, Jr., Houston, both of Tex.

[73] Assignee: Shell Oil Company, Houston, Tex.

[21] Appl. No.: 454,252

[22] Filed: Dec. 21, 1989

[51] Int. Cl.$^5$ .............................................. C07C 6/00
[52] U.S. Cl. ................................. 585/646; 585/666; 585/670
[58] Field of Search ....................... 585/646, 666, 670

[56] References Cited

U.S. PATENT DOCUMENTS

| | | | |
|---|---|---|---|
| 3,261,879 | 7/1966 | Banks | 260/683 |
| 3,340,322 | 5/1967 | Heckelsberg | 260/683 |
| 3,637,892 | 1/1972 | McGrath et al. | 260/683 D |
| 3,726,938 | 4/1973 | Berger | 260/683 D |
| 3,760,026 | 9/1973 | Reusser et al. | 260/683 D |
| 3,786,112 | 1/1974 | Reusser et al. | 260/683 D |
| 3,792,108 | 2/1974 | Arganbright | 260/683 D |
| 3,872,180 | 3/1975 | Nakatomi et al. | 260/683 D |
| 3,933,974 | 1/1976 | Winquist | 423/118 |
| 3,966,883 | 6/1976 | Vaughan et al. | 423/329 |
| 4,000,248 | 12/1976 | Martin | 423/329 |
| 4,017,590 | 4/1977 | Cormier | 423/329 |
| 4,180,524 | 12/1979 | Reusser et al. | 585/644 |
| 4,251,499 | 2/1981 | Nanne et al. | 423/329 |
| 4,335,019 | 6/1982 | Bowes et al. | 502/66 |
| 4,343,692 | 8/1982 | Winquist | 208/111 |
| 4,727,203 | 2/1988 | Hamilton | 585/670 |
| 4,749,819 | 6/1988 | Hamilton | 585/666 |

FOREIGN PATENT DOCUMENTS 1128091 3/1966 United Kingdom .
1205677 9/1970 United Kingdom .

Primary Examiner—Curtis R. Davis
Attorney, Agent, or Firm—Pamela J. McCollough

[57] ABSTRACT

This invention relates to a process for the concurrent isomerization and disproportionation of hydrocarbon olefins by contacting said hydrocarbon at disproportionation conditions with a catalyst comprising an inorganic oxide matrix, a ferrierite compound, and a heavy metal selected from the group consisting of molybdenum, tungsten, rhenium and mixtures thereof.

18 Claims, No Drawings

CONCURRENT ISOMERIZATION AND DISPROPORTIONATION OF OLEFINS

FIELD OF THE INVENTION

This invention relates to a process for the concurrent isomerization and disproportionation of olefinic hydrocarbons utilizing a catalyst comprising an inorganic oxide matrix, a ferrierite compound, an element selected from molybdenum, tungsten, rhenium and mixtures thereof, and optionally, cobalt.

BACKGROUND OF THE INVENTION

Reactions of olefinic molecules in the presence of metal-containing catalysts to produce other olefinic molecules are known in the art as "disproportionation" reactions. A typical olefin disproportionation process is illustrated by U.S. Pat. No. 3,261,879, issued Jul. 19, 1966, to Banks, wherein two similar non-symmetrical molecules of an olefin react in the presence of certain catalysts to produce one olefin of a higher carbon number and one olefin of a lower carbon number such as, for example, propylene disproportionation by the process of U.S. Pat. No. 3,261,879 to produce ethylene and butylenes.

As used in this application, disproportionation process means the conversion of olefinic hydrocarbons into similar olefinic hydrocarbons of higher and lower numbers of carbon atoms per molecule. Where the reactant comprises 1- or 2-olefins having relatively long chains, a mixture of products is obtained comprising primarily olefins having both a larger and a smaller number of carbon atoms than the feed olefin but also including other disproportionated products, for example, saturated hydrocarbons, and other converted and unconverted material. Such an operation is useful in many instances. For example, a more plentiful hydrocarbon can be converted to a less plentiful and therefore more valuable hydrocarbon. One instance of such a conversion occurs when the process of this invention is used to convert both higher and lower molecular weight olefins to olefins in the $C_{10}$-$C_{16}$ range, a range of olefins especially suitable for the manufacture of detergents. Another instance of a disproportionation reaction having considerable value is the disproportionation of propylene to produce ethylene and butene.

A variety of catalysts have been employed for conducting disproportionation reactions, such as those disclosed in U.S. Pat. No. 3,340,322, issued Sep. 5, 1967; U.S. Pat. No. 3,637,892, issued Jan. 25, 1972; U.S. Pat. No. 3,760,026, issued Sep. 18, 1973; U.S. Pat. No. 3,792,108, issued Feb. 12, 1974; U.S. Pat. No. 3,872,180, issued Mar. 18, 1975; and British Patent Specification No. 1,128,091, published Mar. 16, 1966.

It is also known that the presence of a catalyst which possesses double bond isomerization activity in a disproportionation process is advantageous because it increases the rate of conversion and makes possible the production of a wider range of symmetrical olefins such as butene-2. In addition, the isomerization activity permits the exhaustive cleavage of high molecular weight monoolefins with ethylene to lower molecular weight monoolefins such as propylene and isobutene. British Patent No. 1,205,677, published Sep. 16, 1970, provides a catalyst which comprises an olefin disproportionation component and a Group VIII noble metal double bond isomerization component, i.e., palladium, platinum or ruthenium. Another catalyst system which accomplishes the same results is obtained by physically mixing catalytic magnesium oxide with tungsten oxide on silica catalyst. Other catalysts which have been developed include those obtained by copromoting an olefin disproportionation catalyst such as tungsten oxide on silica with minor amounts of the oxides of niobium, tantalum or vanadium to provide the double bond isomerization activity.

U.S. Pat. No. 3,786,112 discloses a catalyst comprising a physical mixture of an olefin disproportionation catalyst and a double bond isomerization catalyst wherein the double bond isomerization catalyst has been treated with an alkali metal or alkaline earth metal compound.

U.S. Pat. No. 4,180,524 discloses a single catalyst composition containing a support, uranium and at least one of molybdenum, tungsten or rhenium, which provides double bond isomerization activity as well as olefin disproportionation activity.

The catalysts in the above references for isomerization and combined isomerization/disproportionation have either basic or neutral isomerization components. It has been found in the present invention that an acidic isomerization component in combination with a disproportionation component can be used for concurrent isomerization/disproportionation with a low side-product make, thus resulting in a greater quantity of useful olefins.

SUMMARY OF THE INVENTION

The present invention relates to a process for the concurrent isomerization and disproportionation of olefinic hydrocarbons which comprises contacting said olefinic hydrocarbons with a catalyst comprising an inorganic oxide matrix, a ferrierite compound, an element selected from the group consisting of molybdenum, tungsten, rhenium and mixtures thereof, and optionally, cobalt.

It has been found that these catalysts show substantially improve branched product yields, i.e. less branching, in a concurrent olefin disproportionation and isomerization process when compared to conventional disproportionation catalysts. In an olefin production process combining the steps of oligomerization, isomerization and disproportionation such as that disclosed in U.S. Pat. No. 3,726,938, issued to Berger, it is preferred to use catalysts prepared according to the instant invention in the disproportionation zone.

DESCRIPTION OF THE PREFERRED EMBODIMENTS

In the process of the instant invention, the concurrent isomerization and disproportionation of an olefinic hydrocarbon is accomplished by contacting the olefinic hydrocarbon with a catalyst comprising an inorganic oxide matrix, a ferrierite compound and an element selected from the group consisting of molybdenum, tungsten, rhenium and mixtures thereof. In a preferred embodiment, the catalyst also contains cobalt.

Olefins which are subjected to isomerization and disproportionation according to the process of this invention include $C_3^+$ olefinic hydrocarbons or $C_3^+$ internal olefins in combination with ethylene. A useful group of feed materials are olefinic hydrocarbons having carbon numbers ranging from $C_2$ to about $C_{100}$ and mixtures thereof, preferably from $C_2$ to about $C_{60}$ and mixtures thereof, and more preferably linear olefinic hydrocarbons having carbon numbers ranging from about $C_4$ to about $C_{40}$ and mixtures thereof. Examples of compounds most suitable for disproportionation according to this invention are acyclic 1- and 2-alkenes, and alkyl and aryl derivatives thereof having from 3 to 20 carbon atoms per molecule. Some specific examples of such olefins are propylene, 1-butene, 2-butene, 1-pentene, 2-pentene, 1-hexene, 2-heptene, 1-octene, 2-nonene, 1-dodecene, 2-tetradecene, 1-hexadecene, 2-methyl-1-butene, 2-methyl-2-butene, 3-methyl-1-butene, 1-phenylbutene-2, and 3-heptene. Higher disproportionation conversions and wider product distributions are obtained at comparable reaction times with 1-olefins than with 2-olefins. 3-olefins are disproportionated at still lower rates.

The feed should be essentially free of impurities which adversely affect the reaction. A subsequent reactivation of the catalyst to remove the effect of such impurities can be made repeatedly by heat treatment with air, using an inert gas to control burn-off temperature.

The catalyst of this invention comprises an inorganic oxide matrix, a ferrierite compound, a heavy metal selected from molybdenum, tungsten, rhenium and mixtures thereof, and optionally, cobalt. In a preferred embodiment, the inorganic oxide matrix and ferrierite compound are comulled and calcined to form a support which is then impregnated with an element selected from the group consisting of molybdenum, tungsten, rhenium and mixtures thereof, and optionally, cobalt.

Suitable inorganic oxide matrices include alumina, silica, silica-alumina, magnesia-alumina, titania-alumina, zirconia-alumina, alumina-titania-zirconia, thoria and the like. In a preferred embodiment, the inorganic oxide matrix is alumina.

The ferrierite compound of the catalyst is typically a synthetic ferrierite which is usually prepared as ammonium aluminosilicate or as an alkali metal aluminosilicate. The alkali metal ion is typically sodium or potassium. The ammonium ferrierite may be converted to the acid form by calcination. The alkali metal aluminosilicate can be converted to the acid form by contacting the alkali metal aluminosilicate with a dilute acid such as 3N or 6N hydrochloric acid. In a preferred embodiment, the ferrierite is added to the inorganic matrix as ammonium ferrierite.

The synthesis of synthetic ferrierite itself may be prepared by a variety of processes. These include, for example, the process described in U.S. Pat. Nos. 3,966,883, 4,000,248 and 4,017,590. A particularly useful process for preparing synthetic ferrierite is described in U.S. Pat. Nos. 3,933,974 and 4,343,692, which disclosures are herein incorporated by reference. Other processes are described in U.S. Pat. No. 4,251,499 and Kibby et al, "Composition and Catalytic Properties of Synthetic Ferrierite", *Journal of Catalysis*, 35, pages 256–272 (1974).

The prominent structural features of synthetic ferrierite have been found by X-ray crystal structure determination to be parallel channels in the aluminosilicate framework. The term "ferrierite compound", as used herein, refers to a two dimensional zeolite consisting of intersecting 8 and 10 ring channels. The larger 4.3Å×5.5Å ten ring channel parallels the c crystallographic axis, while the smaller 3.4Å×4.8Å eight ring channel parallels the b crystallographic axis. Practically speaking, the larger ten ring channel is the only diffusion path available to a molecule of any moderate size. Therefore, the channel system of ferrierite is essentially unidimensional due to practical considerations.

The ferrierite is typically comulled with the inorganic oxide matrix in the form of a powder in an amount sufficient to yield a final catalyst having from about 1 percent by weight to about 70 percent by weight, preferably from about 2 by weight to about 40 percent by weight, and more preferably from about 5 percent by weight to about 25 percent by weight of ferrierite. While it is preferable that the ferrierite be comulled with the inorganic oxide matrix prior to the addition of the metal components, the ferrierite may be added to the inorganic oxide matrix at the same time as the metals or after the metals have been added to the inorganic oxide matrix.

After the inorganic oxide matrix and the ferrierite are mixed together, the mixture is typically dried and calcined at a temperature in the range of from about 300° C. to about 600° C. to form a support onto which molybdenum and/or tungsten and, optionally, cobalt can be incorporated. The molybdenum and/or tungsten, and/or rhenium, and optionally, cobalt can be incorporated onto the support by any suitable method including, for example, coprecipitation, dry mixing and impregnation, with impregnation being preferred.

In a preferred embodiment, the catalyst in the instant invention contains cobalt and molybdenum and is prepared by impregnating an alumina/ferrierite support with an impregnation solution prepared by dissoloving cobalt salts and molybdenum salts in an ammoniacal solution. A wide range of cobalt salts are suitable, such as cobalt nitrate, cobalt carbonate, cobalt hydroxide, cobalt acetate, cobalt oxalate, or cobalt oxide. The preferred cobalt salts are cobalt nitrate and cobalt carbonate. Suitable molybdenum salts include molybdenum oxide such as ammonium heptamolybdate or ammonium dimolybdate. Hydrogen peroxide may also be used to aid in solution preparation in some cases. Optionally, a suitable soluble amine compound such as monoethanolamine, propanolamine or ethylenediamine may be added to the impregnation solution in order to aid in stabilization of the solution.

Following the addition of the metals to the alumina/ferrierite support, the resulting material is dried and calcined. Drying is accomplished by conventional means. It may be carried out by forced draft drying, vacuum drying, air drying or similar means. Drying temperatures are not critical and depend upon the particular means utilized for drying. Drying temperatures will typically range from about 50° C. to about 150° C.

After drying, the material is calcined to produce the finished catalyst. The material may be calcined in an oxidizing or neutral atmosphere, although air is preferred. However, if binders and/or lubricants are used the material is heated in an oxygen-containing atmosphere, preferably air, in order to burn out the binders and lubricants. Calcining temperatures will typically range from about 300° C. to about 600° C. Burn-out temperatures will depend on the concentration of oxygen in the burn-out atmosphere as well as the burn-out time involved. Typically, burn-out temperatures will range from about 300° C. to about 600° C. Drying, calcining and burn-out may be combined in one or two steps. Most frequently the calcining and/or burn-out steps are combined using an oxygen-containing atmosphere.

The final catalysts are typically found to have surface areas greater than about 200 m²/g. In general, the metals contents of the final catalysts range from about 8 percent by weight to about 18 percent by weight, preferably from about 10 percent by weight to about 14 percent by weight molybdenum, from about 10 percent by weight to about 32 percent by weight, preferably from about 18 percent by weight to about 26 percent by weight tungsten, or from about 0.1 percent by weight to about 20 percent by weight, preferably from about 0.5 percent by weight to about 10 percent by weight rhenium. The catalyst typically contains from about 1 percent by weight to about 70 percent by weight, preferably from about 2 percent to about 40 percent by weight ferrierite. When the catalyst contains cobalt, the final catalyst generally contains from about 0.1 percent by weight to about 5 percent by weight cobalt, preferably from about 2.5 percent by weight to about 4 percent by weight cobalt.

The process of the invention can be carried out either batchwise or continuously, using a fixed catalyst bed, or a stirrer equipped reactor or other mobile catalyst contacting process as well as any other well known contacting technique. Preferred reaction conditions, e.g., temperature, pressure, flow rates, etc., vary somewhat depending upon the specific catalyst composition, the particular feed olefin, desired products, etc. The process is carried out at temperatures ranging from about 10° C. to about 350° C. and at pressures in the range of about 50 psig to about 500 psig. The disproportionation reaction is usually effected in a liquid phase in the presence of a small amount of ethylene and if desired, liquid reaction diluents are utilized. Examples of suitable diluents are hydrocarbons free from aliphatic unsaturation, such as acyclic or alicyclic alkanes of from 6 to 12 carbon atoms, i.e. hexane, isooctane and cyclohexane. Also exemplary would be monoaromatic compounds such as benzene and toluene. If the diluent is added, it is present in amounts up to 20 moles of diluent per mole of olefinic reactants.

The operable range of contact time for the process of this invention depends primarily upon the operating temperature and the activity of the catalyst, which is influenced by surface area, promoter concentration, activation temperature, etc. In general, the distribution of products is not drastically altered by variation in contact time. Shorter contact times are usually associated with higher temperatures, but, when larger amounts of higher molecular weight products are desired, a suitable combination of contact time and temperature is selected. With proper selection of conditions and contact times, very high efficiency of conversion to desired products can be obtained.

In this application, space rates are given in WHSV (weight hourly space velocity; weight of reactant feed per weight of catalyst per hour).

With a fixed bed reactor, continuous flow operation at pressures in the range of about 50 psig to about 500 psig, preferably about 150 psig to about 250 psig, with catalysts having densities ranging from about 0.5 gram per cc to about 1.0 gram per cc and surface areas greater than about 300 m$^2$/g, and at temperatures in the range of about 10° C. to about 350° C., preferably about 100° C. to about 250° C., weight hourly space velocities in the range of about 0.1 to about 10.0 parts by weight of olefinic hydrocarbon feed per part by weight of catalyst per hour are suitable. The space velocity is adjusted according to changes in density of feed due to change of pressure or temperature, and variation in reaction temperature and the activity of the catalyst. The higher space velocities in general are associated with higher reaction temperatures.

The catalyst of the present invention is advantageous with respect to a catalyst in which the olefin feed is only disproportionated rather than isomerized and disproportionated concurrently in that a different mixture of product olefins is obtained. The ability to shift the mixture of product olefins is particularly useful in maximizing the economic return from any given olefin feedstock.

The ranges and limitations provided in the instant specification and claims are those which are believed to particularly point out and distinctly claim the instant invention. It is, however, understood that other ranges and limitations that perform substantially the same function in substantially the same manner to obtain the same result are intended to be within the scope of the instant invention as defined by the instant specification and claims.

The process of the instant invention will be further described below by the following examples which are illustrative and which are not to be construed as limiting the invention.

ILLUSTRATIVE EMBODIMENTS

Catalyst Preparation

Catalyst A

A 10% ferrierite/alumina catalyst support was prepared as follows. Alpha-alumina monohydrate (1195.2 grams, 900 grams dry weight basis) and ammonium ferrierite (105 grams, 100 grams dry weight basis) were mulled in a Lancaster muller bowl along with a dilute acetic acid solution (20 grams glacial acetic acid in 807 grams water) for 45 minutes. This mull mix was extruded using a conventional Bonnot extruder. The extrudate was dried at 150° C. for several hours, followed by careful calcination in air via a 3° C./minute ramp from 120° C. to 500° C. The catalyst support was held at 500° C. for two hours.

This 10% ferrierite/alumina support (75 grams, H$_2$O pore volume was 0.68 cc/g) was impregnated with a Co/Mo solution prepared by combining cobalt carbonate (5.78 grams), ammonium dimolybdate (12.86 grams), and enough aqueous ammonia to bring the volume to 51 ml. The catalyst was impregnated in small portions with extensive agitation. The catalyst was dried at 150° C. and calcined as above. The properties of the catalyst are listed in Table I.

Catalyst B

Catalyst B was prepared using a conventional dry pore volume impregnation technique. A solution suitable for impregnating 75 grams of calcined alumina support with a pore volume of 0.69 cc/g was prepared as follows. An impregnation solution was made by combining 5.78 grams of cobalt nitrate, 12.86 grams of ammonium dimolybdate and enough 24% aqueous ammonia to bring the solution to a total volume of 51 milliliters. After adding the entire solution to the alumina support in several small portions with intermediate agitations, the impregnated support was dried overnight at 150° C. and calcined in air for 2 hours at 450° C. The properties of the catalyst are listed in Table I.

Catalyst Testing

Catalysts A and B were each tested utilizing the following procedure. Twenty ccs of 16-45 mesh catalyst particles diluted 1/1 with 80 mesh SiC are charged to a stainless steel reactor to obtain a bed length of 8 inches. The catalyst is heated at a temperature of 550° C. under flowing nitrogen for 12 hours to remove any residual water from the catalyst. The catalyst is then cooled to 250° F. and feed is introduced at a weight hourly space velocity (WHSV) of 1.0. The feed for these reactions is an equilibrium mixture of decenes prepared by the isomerization of 1-decene. The feed contains approximately 1.5% branched decenes. The results of catalyst testing are presented in Table II.

As mentioned previously, catalysts prepared by the process of the instant invention have improved selectivity to linear olefins, higher conversion rates and a wider range of reaction products than conventionally prepared disproportionation catalysts. Values in the "Product Branching" section in Table II represent the relative amount of branched olefins in the product stream and are reported relative to the conventionally prepared catalyst, which is shown as 1.00. A value of less than 1.00 would indicate fewer branched olefins in the product stream and thus a more selective and hence more desirable catalyst. Values in the Carbon Number Distribution section of Table II are reported in normalized weight percent. It is clear from the data in Table II that shifts in the overall product distribution are seen when Catalyst A, the mixed isomerization/disproportionation catalyst prepared according to the invention, is used. In addition, when Catalyst A according to the invention is utilized, less of the more valuable linear olefins are converted into branched olefins, which are less valuable and thus, undesired side products.

TABLE I

| Catalyst Properties | | |
|---|---|---|
| Catalyst | A | B |
| % wt. Molybdenum[a] | 8.1 | 8.1 |
| % wt. Cobalt[b] | 3.2 | 3.2 |
| % wt. Ferrierite[c] | 8.6 | — |
| Surface Area[d] $m^2$/gm | 272 | 250 |
| Pore Volume[e] cc/gm | 0.48 | 0.52 |
| Compacted Bulk Density[f] gm/cc | 0.76 | 0.79 |

[a] Weight percent determined by neutron activation analysis or atomic absorption spectroscopy.
[b] Weight percent determined by neutron activation analysis or atomic absorption spectroscopy.
[c] Weight percent determined by neutron activation analysis or atomic absorption spectroscopy.
[d] BET, by nitrogen adsorption/desorption. Micromeritics Digisorb 2500 Instrument.
[e] By nitrogen adsorption, Micromeritics Digisorb 2500 Instrument.
[f] 209 cc volume fully settled in a graduated cup and weighed.

TABLE II

| Catalyst | A | B |
|---|---|---|
| Catalyst Test Results | | |
| $C_{10}$ Feed Iso. | $C_{10}$ | Iso. $C_{10}$ |
| Reaction Temperature, °F. | 250 | 250 |
| Catalyst Volume, cc | 20 | 20 |
| Catalyst Weight, gm | 15.2 | 13.4 |
| WHSV | 1.0 | 1.5 |
| Product Branching | | |
| | 0.29 | 1.00 |
| Carbon Number Distribution | | |
| $C_2$ | 0.000 | 0.000 |
| $C_3$ | 0.945 | 0.027 |
| $C_4$ | 1.835 | 0.743 |
| $C_5$ | 3.834 | 1.646 |
| $C_6$ | 5.823 | 3.574 |
| $C_7$ | 7.930 | 5.693 |
| $C_8$ | 10.185 | 8.166 |

TABLE II-continued

| Catalyst | A | B |
|---|---|---|
| $C_9$ | 12.729 | 10.542 |
| $C_{10}$ | 12.573 | 13.817 |
| $C_{11}$ | 11.925 | 13.053 |
| $C_{12}$ | 10.390 | 12.281 |
| $C_{13}$ | 8.418 | 10.345 |
| $C_{14}$ | 6.013 | 8.091 |
| $C_{15}$ | 3.783 | 5.462 |
| $C_{16}$ | 1.961 | 3.290 |
| $C_{17}$ | 1.339 | 1.454 |
| $C_{18}$ | 0.216 | 0.721 |
| $C_{19}$ | 0.036 | 0.414 |
| $C_{20}$ | 0.051 | 0.245 |
| $C_{21}$ | 0.010 | 0.243 |
| $C_{22}$ | 0.006 | 0.057 |
| $C_{23}$ | 0.000 | 0.063 |
| $C_{24}$ | 0.000 | 0.026 |
| $C_{25}$ | 0.000 | 0.018 |
| $C_{26}$ | 0.000 | 0.012 |
| $C_{27}$ | 0.000 | 0.011 |
| $C_{28}$ | 0.000 | 0.007 |

What is claimed is:

1. A process for the concurrent isomerization and disproportionation of olefinic hydrocarbons having carbon numbers ranging from $C_2$ to about $C_{100}$ which comprises contacting said olefins with a catalyst comprising an inorganic oxide matrix, a ferrierite compound, and a heavy metal selected from the group consisting of molybdenum, tungsten, rhenium and mixtures thereof.

2. The process of claim 1 wherein said inorganic oxide matrix is selected from alumina, silica, silica-alumina, magnesia-alumina, titania-alumina, zirconia-alumina, alumina-titania-zirconia, and thoria.

3. The process of claim 2 wherein said inorganic oxide matrix is alumina.

4. The process of claim 1 wherein said catalyst contains from about 8 percent by weight to about 32 percent by weight heavy metal.

5. The process of claim 4 wherein said catalyst contains from about 8 percent by weight to about 18 percent by weight molybdenum.

6. The process of claim 1 wherein said catalyst contains from about 1 percent by weight to about 70 percent by weight ferrierite compound.

7. The process of claims 1 wherein said catalyst contains from about 2 percent by weight to about 40 percent by weight ferrierite compound.

8. The process of claim 1 wherein said olefinic hydrocarbons have carbon numbers ranging from $C_2$ to about $C_{60}$.

9. The process of claim 1 wherein said process is carried out at a temperature in the range of from about 10° C. to about 350° C. and a pressure in the range of from about 50 psig to about 500 psig.

10. A process for the concurrent isomerization and disproportionation of olefinic hydrocarbons having carbon numbers ranging from $C_2$ to about $C_{100}$ which comprises contacting said olefinic hydrocarbons with a catalyst comprising an inorganic oxide matrix, a ferrierite compound, cobalt and a heavy metal selected from the group consisting of molybdenum, tungsten, rhenium and mixtures thereof.

11. The process of claim 10 wherein said inorganic oxide matrix is selected from alumina, silica, silica-alumina, magnesia-alumina, titania-alumina, zirconia-alumina, alumina-titania-zirconia, and thoria.

12. The process of claim 11 wherein said inorganic oxide matrix is alumina.

13. The process of claims 10 or 11 wherein said catalyst contains from about 0.1 percent by weight to about 5 percent by weight cobalt and from about 8 percent by weight to about 32 percent by weight heavy metal.

14. The process of claims 10 or 11 wherein said catalyst contains from about 2.5 percent by weight to about 4 percent by weight cobalt and from about 8 percent by weight to about 18 percent by weight molybdenum.

15. The process of claims 10 or 11 wherein said catalyst contains from about 1 percent by weight to about 70 percent by weight ferrierite compound.

16. The process of claims 10 or 11 wherein said catalyst contains from about 2 percent by weight to about 40 percent by weight ferrierite compound.

17. The process of claim 10 wherein said olefinic hydrocarbons have carbon numbers ranging from $C_2$ to about $C_{60}$.

18. The process of claim 10 wherein said process is carried out at a temperature of from about 10° C. to about 350° C. and a pressure of from about 50 psig to about 500 psig.

* * * * *